(12) United States Patent
Helle et al.

(10) Patent No.: US 9,259,560 B2
(45) Date of Patent: Feb. 16, 2016

(54) BRACHYTHERAPY ARRAY PREPARATION DEVICE

(75) Inventors: Kevin Helle, Bartlett, IL (US); Jay Reed, Elk Grove, IL (US); George Pittman, Louisburg, NC (US); Lory Bradley, Princeton, NJ (US)

(73) Assignee: Medi-Physics, Inc., Princeton, NJ (US)

( * ) Notice: Subject to any disclaimer, the term of this patent is extended or adjusted under 35 U.S.C. 154(b) by 1339 days.

(21) Appl. No.: 12/166,417

(22) Filed: Jul. 2, 2008

(65) Prior Publication Data

US 2009/0012347 A1 Jan. 8, 2009

Related U.S. Application Data

(60) Provisional application No. 60/947,583, filed on Jul. 2, 2007.

(51) Int. Cl.
*A61M 37/00* (2006.01)
*A61N 5/10* (2006.01)

(52) U.S. Cl.
CPC ......... *A61M 37/0069* (2013.01); *A61N 5/1027* (2013.01); *A61N 2005/1009* (2013.01); *A61N 2005/1023* (2013.01)

(58) Field of Classification Search
CPC ....... A61M 36/12; A61M 36/00; A61M 5/00; A61N 5/00; A61N 5/12; A61B 17/00
USPC .......................................... 600/1–8
See application file for complete search history.

(56) References Cited

U.S. PATENT DOCUMENTS

| | | | |
|---|---|---|---|
| 4,427,005 A * | 1/1984 | Tener | 606/186 |
| 5,030,195 A | 7/1991 | Nardi | |
| 5,772,574 A * | 6/1998 | Nanko | 600/1 |
| 6,752,753 B1 * | 6/2004 | Hoskins et al. | 600/7 |
| 2004/0059177 A1 * | 3/2004 | Baltas et al. | 600/3 |
| 2004/0116767 A1 * | 6/2004 | Lebovic et al. | 600/7 |

* cited by examiner

*Primary Examiner* — Christine H Matthews

(57) ABSTRACT

A device for manufacturing a brachytherapy array having a planar base which includes a working area comprising at least one planar major surface defining a first array of apertures, and a holding mechanism for holding a planar surgical mesh over the working area of said planar base. Also, a method for forming a brachytherapy array using this device.

17 Claims, 7 Drawing Sheets

BRACHYTHERAPY ARRAY PREPARATION DEVICE

FIELD OF THE INVENTION

The present invention relates to the field of brachytherapy devices. More specifically, the present invention is directed to a device and method of making a brachytherapy array.

BACKGROUND OF THE INVENTION

There are clinical applications of I-125 seeds that involve sewing Seed-In-Carrier (SIC) material into a surgical mesh before implanting into a patient. The SIC typically includes a plurality of brachytherapy seeds within an elongate carrier material. The clinical applications of these mesh products can include removal of a cancerous tumor and then the overlay of this surgical mesh for radiation treatment to further treat the patient. The surgical mesh is commonly prepared by hand in the operating room by the Radiation Oncologist, and is based on several pieces of information gained during the surgical procedure including: target site, size of the surgical margin, and many other factors.

The current preparation of the mesh is done by measuring the surgical mesh, marking the mesh for seed placement, placing the mesh on a soft and pliable surface, creating pocket holes for the weaving of the SIC material, sewing in the SIC, anchoring the SIC on each end of the mesh, and applying anchors (corners and center of mesh) for implant anchoring into the patient. This is a time-consuming procedure which prolongs the exposure to the radiation from the SIC.

There is therefore a need for a device and method for making a brachytherapy array which offers a convenience to physicians preparing a brachytherapy array. There is also a need for a device and method for easing the clinical requirements of developing lung therapy devices. There is further a need for reducing the time required for preparing a brachytherapy array and reducing the occupational radiation exposure when preparing a brachytherapy array.

SUMMARY OF THE INVENTION

The present invention provides an array preparation device that can replace the current methods of preparing a surgical brachytherapy mesh.

DETAILED DESCRIPTION OF THE PREFERRED EMBODIMENTS

Figure 1:
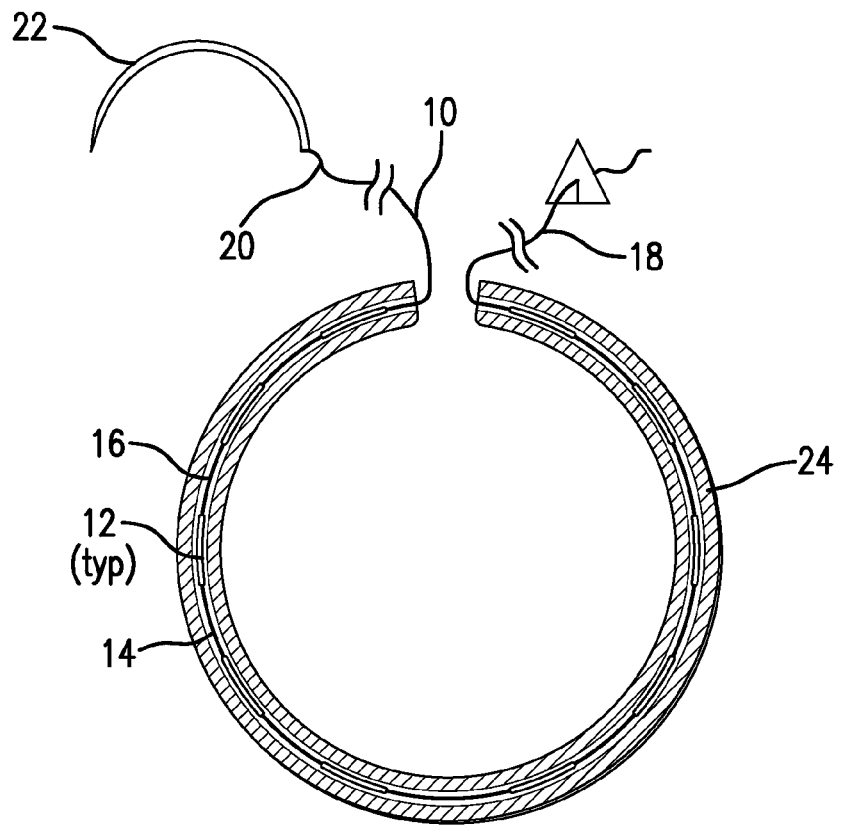
FIG. 1 depicts a schematic for seed-in-carrier (SIC) product of the prior art within a shielding ring.

A Seed-In-Carrier 10 as known in the art is shown in FIG. 1. SIC 10 consists of 10 brachytherapy seeds 12 placed inside an elongate hollow absorbable braided carrier 14. Braided carrier 14 defines an elongate hollow core 16 allowing for seeds 12 to be placed and held therein. SIC 10 does not have solid spacers inserted into the voids between the seeds as the RS, a some seed-in-carrier products do, enabling SIC 10 to be more flexible in use, and thus ideal for sewing into treatment areas. This product is also ideal for certain clinical applications, specifically external treatment.

Figure 2:
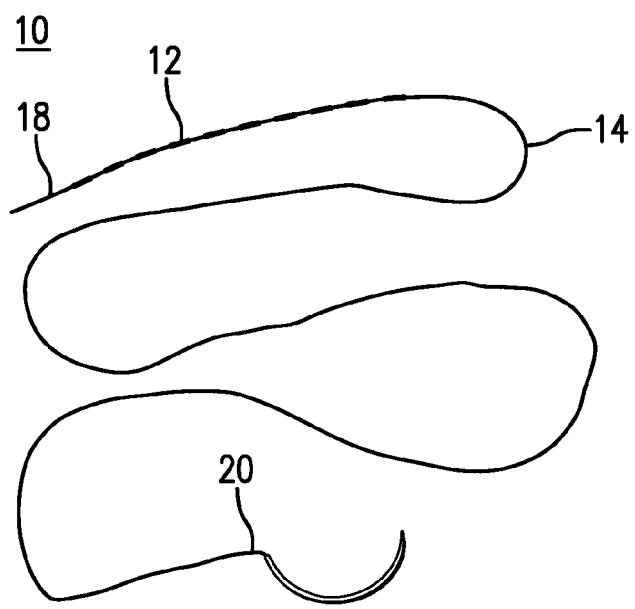
FIG. 2 depicts the seed-in-carrier assembly of FIG. 1 removed from the shielding ring.

With additional reference to FIG. 2, SIC 10 is supplied as a length of bio-absorbable braided carrier 14, or suture, having opposed ends 18 and 20. Carrier 14 accommodates ten (10) brachytherapy seeds 12 inserted into core 16 through first end 18. Second end 20 is threaded through, or otherwise attached to, an arcuate needle 22. Seeds 12 are typically spaced in a linear fashion at a 1 cm spacing center to center (or 5.5 mm in between 4.5 mm seeds). The device is then placed into SST ring 24 for shielding purposes, and then packaged into a semi-permeable package (not shown) and sterilized.

For certain therapy applications it is desirable to arrange several SIC segments into a surgical mesh, and then clinically apply the prepared mesh into the patient. The present invention is directed to a device and method of preparing such a mesh as described hereinbelow.

Needle 22 is used with the array preparation device 100 of the present invention to prepare a brachytherapy array. SIC 10 is desirably delivered sterile, thus this array preparation device desirably allows for the aseptic assembly of sterile components for biological implantation of a class 2 permanently implanted medical device. As shown, seeds 12 are imbedded into the bio-absorbable carrier 14 at end 18, opposite end 20 with the needle. This allows for "sewing" of SIC 10 into the surgical site, as well as into a mesh for the creation of an array of brachytherapy devices.

Figure 3:
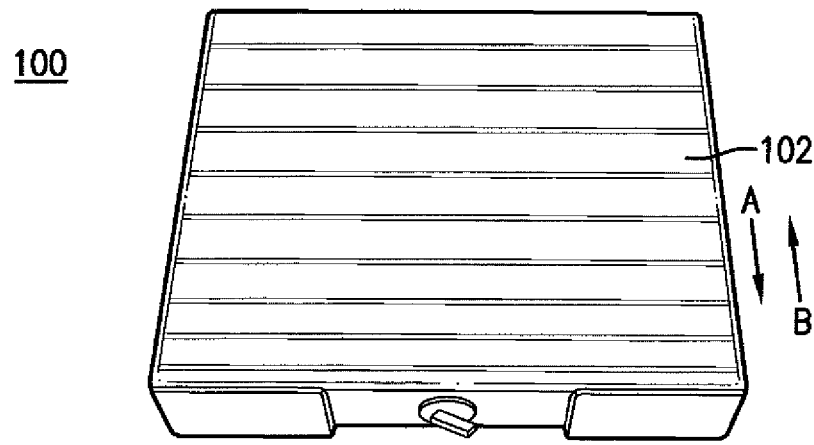
FIG. 3 depicts a device of the present invention for making a brachytherapy array.

Array Preparation Device 100 is shown in FIG. 3 with its removable cover 102 in place over body 106. Cover 102 and body 106 are desirably formed from a radiation-attenuating material and cooperatively engage each other so as to provide a shield for protecting an operator or user from the radiation of a brachytherapy SIC used in forming an array with device 100. Cover 102 and body 106 are desirably made with a non-magnetic stainless steel (such as 304 and/or 316) and may include plastics such as Delrin on at least some of those surfaces exposed to a user. Cover 102 protects device 100. It is also used as a movable sliding shield tray to protect the user from radiation exposure while preparing the surgical mesh for implant. Cover 102 slides forward and backward (shown by arrows A and B) to reveal and cover, respectively, the actual working area of the device. When building the brachytherapy array the cover is first advanced clear of the working area to begin. As each row of SIC 10 is sewn into the mesh the cover is incrementally advanced back to cover the portions of the mesh having an attached SIC and thus protect the operator until the mesh is completed, at which point cover 102 may be fully positioned over device 100 as shown in FIG. 3. Cover 102 desirably remains in place over the assembled mesh, shielding the OR staff, until the mesh is required for the procedure.

Figure 4:
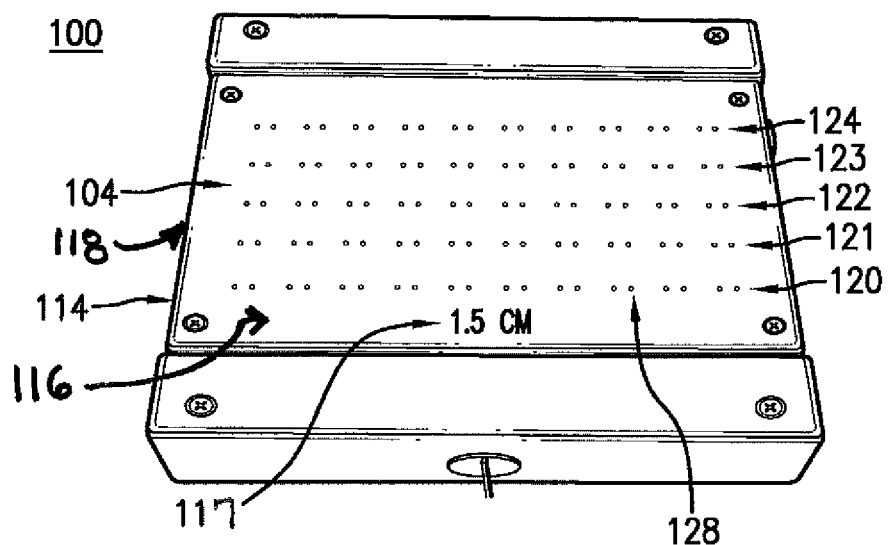
FIG. 4 depicts the device of FIG. 3 with its cover removed.
Figure 5:
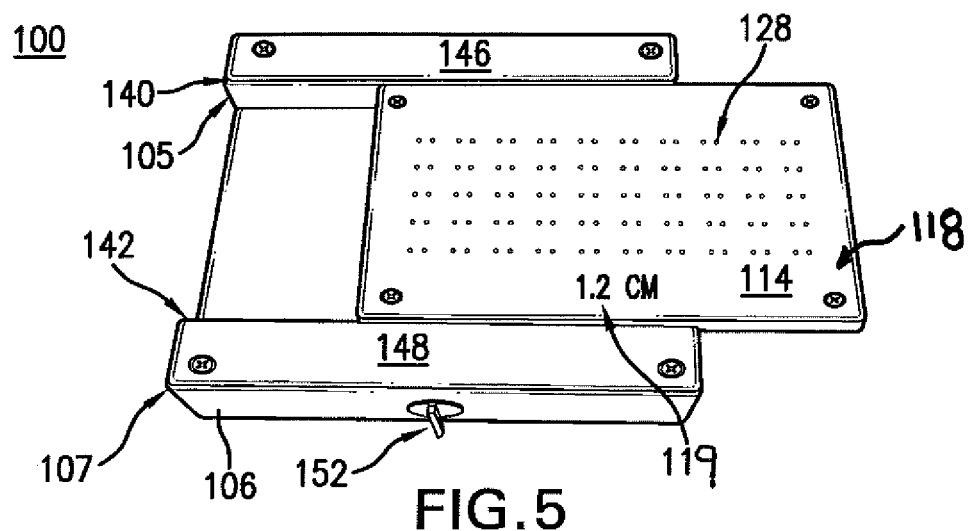
FIG. 5 depicts the ability of the center tray of the device of FIG. 3 to slide from the housing.

After cover 102 is removed the working area 104 of device 100 is exposed, as shown in FIG. 4. Device body 106 includes elongate ridges 105 and 107 in facing opposition and defining an elongate open channel 108 communicating between opposed open ends 110 and 112. Channel 108 receives an elongate planar tray 114 which may be slid in and out thereof so as to position tray 114 in working area 104. Tray 114 includes major face 116 define rows 120, 121, 122, 123, and 124 of apertures 128 corresponding to the locations of thread holes to be formed in a mesh as will be described hereinbelow. Tray 114 further includes an opposed major face 118 which will similarly define rows of apertures of a different spacing than major face 116. As shown in FIG. 5, tray 114 slides in and out of position so that it can be reversed to expose either major face 116 or 118. When in position, tray 114 is desirably securely held in channel 108, such as by cooperating mechanical detents of body 106 and tray 114 (not shown) although other known means may be employed.

Tray 114 desirably is marked with a reference such as '1.5' 117 or '1.2' 119 to represent the vertical spacing between adjacent SIC rows 120, 121, 122, 123, and 124. The present invention contemplates that the spacing of these rows as provided by tray 114 will suit the clinical needs for the final mesh product. The intent is to identify common, or standard, measurement(s) that can be provided in advance of the procedure so that tray 114 may be used to create the required spacing. The references 117, 119 can be machined or laser-etched and is desirably easily readable through the mesh during use of device 100 so as to further ensure the operator is forming a mesh with appropriately-spaced SIC's. Whereas FIG. 4 depicts the 1.5 cm 117 side 116 of tray 114, FIG. 5 depicts the opposed 1.2 cm 119 side 118 of tray 114. Tray 114, with its reference marks 117, 119 and apertures 128, functions both as a standard reference for planning, and also as a functional aspect with relation to sewing the SIC into the mesh. As will be clear to the user, apertures 128 can be used for an entire SIC product (10 seeds across), multiple SIC products using numerous horizontal reference locations, or a portion of SIC product(s) using <10 seeds per row.

Figure 9:
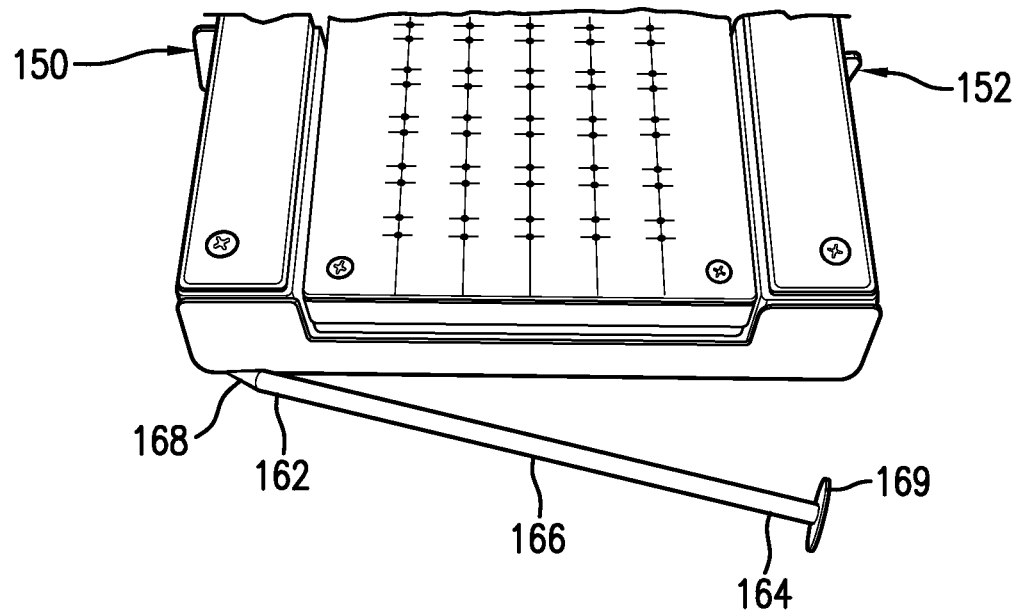
FIG. 9 depicts a tool for punching holes through the surgical mesh and its storage area in the device.

The surgical mesh 200 can be supplied in many sizes and materials, but is commonly supplied as a 12 inch by 12 inch patch. The surgical mesh is desirably cut so that opposed edges will span across a major face of tray 114 and be engaged by a holding mechanism which holds the mesh over working area 104. In this embodiment, the holding mechanism is provided by clamps 146 and 148 as herein described. One or both of the opposed edges of the mesh are insertable into one or both of first and second edge channels 140 and 142, respectively. Edge channel 140 is defined between ridge 105 of product body 106 and a planar clamp 146. Clamp 146 is urgeable towards and away from ridge 105 so as to hold and release, respectively, one edge of a mesh inserted into channel 140. Similarly, edge channel 142 is defined between ridge 107 of product body 106 and a planar clamp 148. Clamp 148 is urgeable towards and away from ridge 107 so as to hold and release, respectively, one edge of a mesh inserted into channel 142. Each of clamps 146 and 148 is operably linked to a cam knob 150 and 152 (as shown in FIG. 9), respectively. Cam knobs 150 and 152 each turn a simple cam linkage within product body 106 so as to operate their respective clamps.

Figure 6:
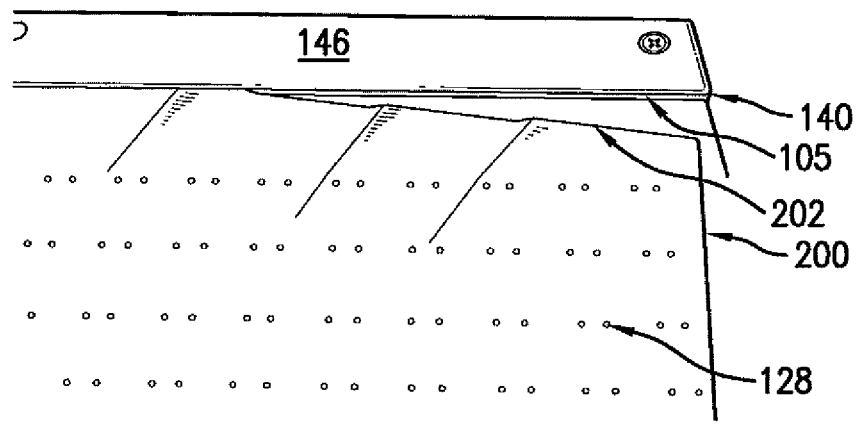
FIG. 6 depicts a surgical mesh being positioned with respect to the cam-activated hold-down.
Figure 7:
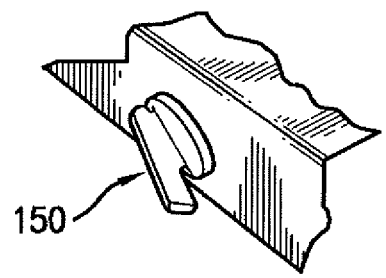
FIG. 7 depicts the knob for turning the cam.

As shown in FIG. 6, a first edge 202 of a surgical mesh 200 is inserted into edge channel 140. Cam knob 150 is then turned to urge clamp 146 against first ridge 105 to thereby lock edge 202 of mesh 200 in position. Then the opposing edge of mesh 200 will be inserted into edge channel 142 so that cam knob 152 (highlighted in FIG. 7) may be turned to urge clamp 148 against second ridge 107. Desirably, the exposed major surface of tray 114 will extend higher than each of ridges 105 and 107 so that operation of the clamps will help pull mesh 200 taught over tray 114, making it easier for an operator to subsequently punch holes through mesh 200, although it is also contemplated by the present invention that ridges 105 and 107 may be differently oriented with respect to tray 114. Alternatively, the present invention contemplates other conventional methods for holding mesh 200 across tray 114 may be employed rather than cam-operated clamps. For example, an elastic band or other snug-fitting framing device may be secured about the perimetrical edges of tray 114 to hold mesh 200 across the appropriate major surface of tray 114. Regardless of the method used, after securing mesh 200, the underlying reference apertures 128 of tray 114 are contemplated to be easily visible through mesh 200.

Figure 8:
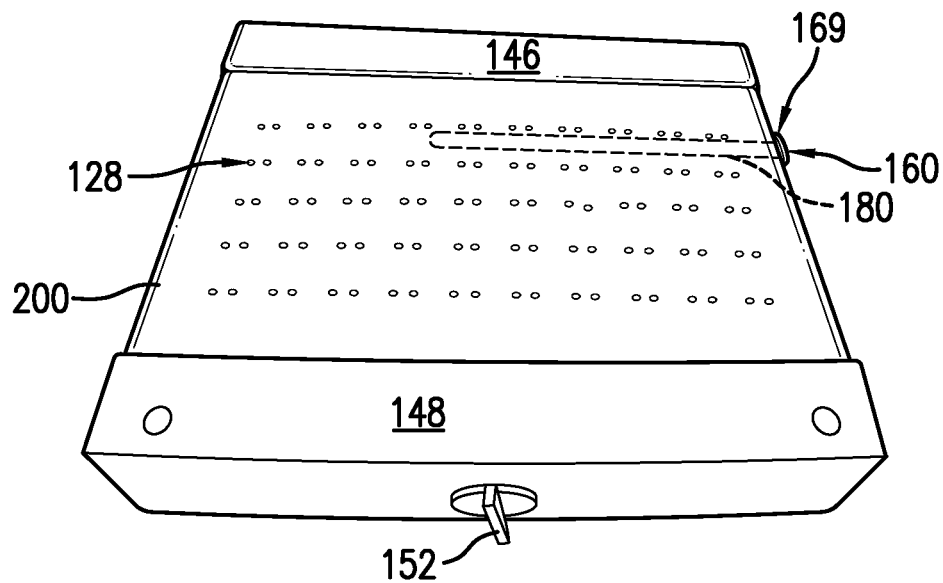
FIG. 8 depicts the surgical mesh locked in place.

FIGS. 8 and 9 depict an elongate punch tool 160 that stores within reference tray 114. Punch tool includes a first end 162, an opposed second end 164, and an elongate body 166 extending therebetween. First end 162 desirably includes a bevelled tip 168 to provide a pointed end for punching through a mesh affixed across tray 114. Punch tool 160 thus may form holes 204 in mesh 200 corresponding to the array of apertures 128 of tray 114. The size and spacing of holes 204 thereby aid the user in sewing the SIC into the desired locations. Tray 114 defines an elongate chamber 180 (shown by phantom lines in FIG. 8) into which bevelled tip and body 166 of punch tool 160 may be stored. Second end 164 of punch tool may include a transversely extending tool head 169 for abutting against tray 114 and aiding handling of punch tool 160. Punch tool 160 thus fits into the side of tray 114, and is held in place until needed for use.

Figure 10:
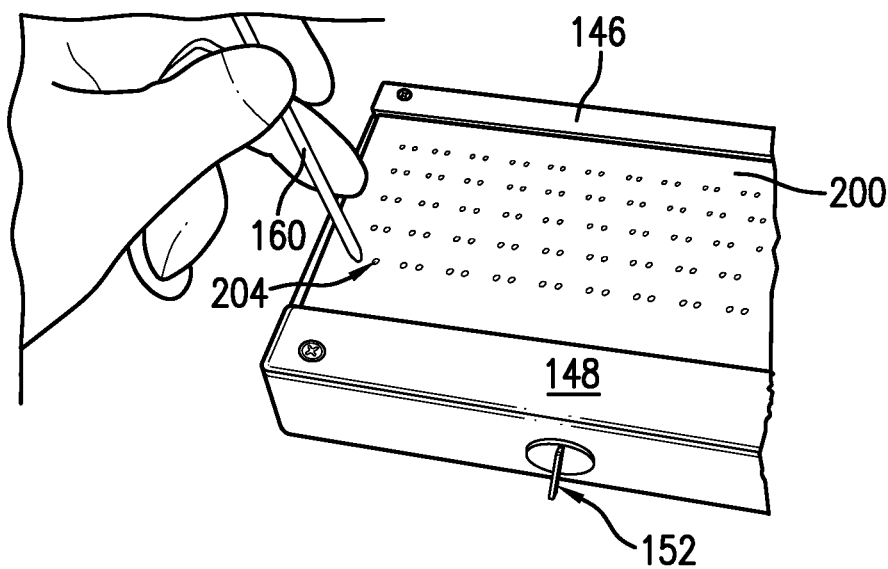
FIG. 10 depicts a hole being punched through the mesh.

FIG. 10 depicts how holes 204 are made in the desired positions, by pressing the tool through surgical mesh 200, into the underlying reference tray 114. There is typically an audible pop when the tool breaks through the fibers of the mesh. Holes 204 are large enough to sew the largest diameter of SIC 10, the seed component, through the mesh. The present invention also contemplates that multiple tool heads, or tips, may be provided on a planar support so that all of the holes may be punched in a single action. Additionally, there could be a cam action to implied the tool tips into the mesh as a single action, creating all of the holes needed for that particular mesh preparation.

Figure 11:
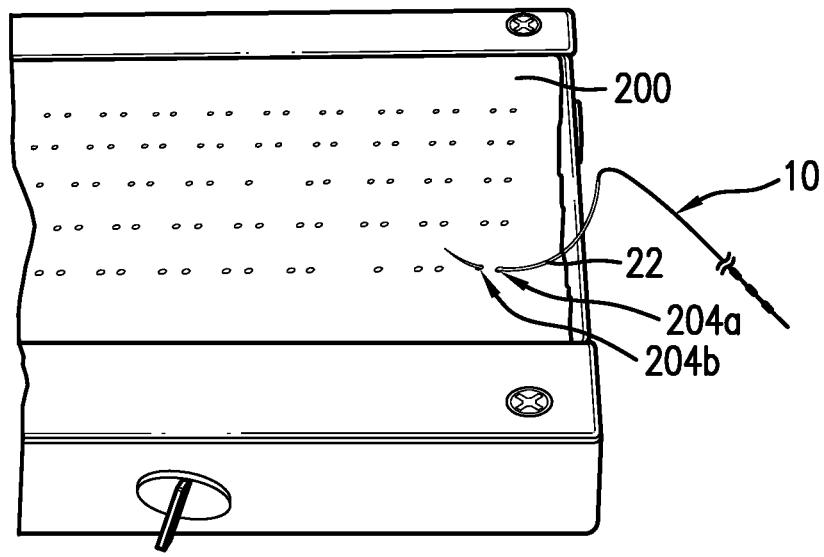
FIG. 11 depicts an SIC being threaded through a line of punched holes in the array.

Next, as shown in FIG. 11, SIC 10 is sewn into the taught and hole-laden surgical mesh. The curvature of needle 22 allows the user to sew down into a first hole 204a, up through a second hole 204b, and then pull through until a seed 22 is left in the desired position between the holes. The seed is actually deposited on the underside of the mesh, and that is desirable for securing the ends 16 and 18 of SIC 10 to mesh 200.

Figure 12:
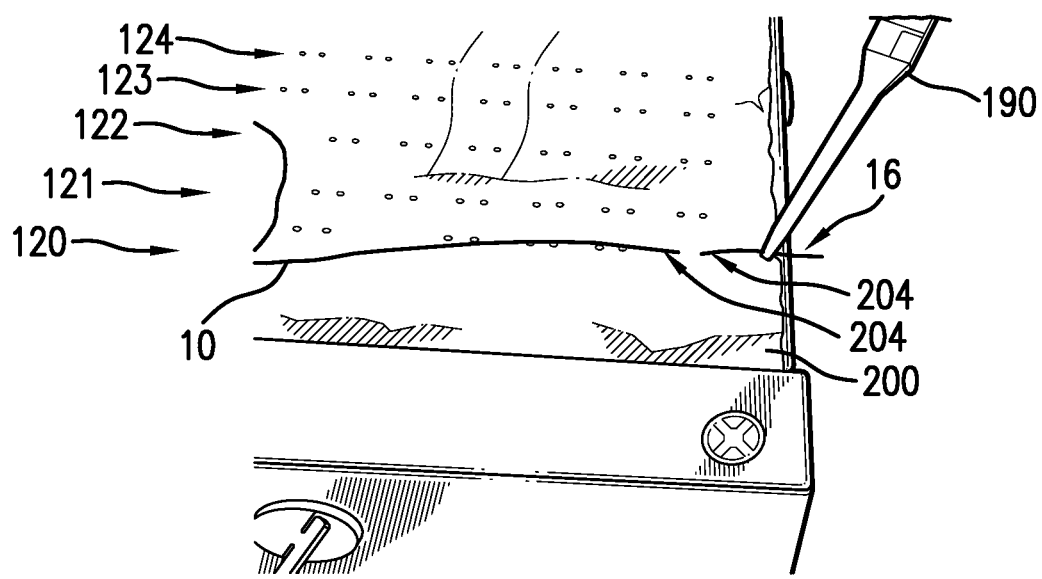
FIG. 12 depicts the securing one end of the SIC in the mesh.

As shown in FIG. 12, after pulling a SIC 10 through the appropriate holes 204, it is common to secure end 16 of SIC 10 to mesh 200 to thereby keep from pulling through the mesh on subsequent sewing steps. This can be accomplished with reverse forceps 190 or any other type of temporary mechanical fastener. The present invention further contemplates that the device includes clamping devices on the leading (or start sewing) edges of the device for performing this function.

End 18 of SIC 10 will be secured to mesh 200 after SIC 10 has been completely sewn in to its respective row 120, 122, or 124 of apertures 128, or its desired orientation. Clamping devices may be provided at this end also. Ends 16 and 18 of SIC 10 may then be affixed to mesh 200 using known fastening methods or devices, such as surgical staples, cyanoacrylate, coseal, or other biologically compatible materials that are currently used for securing these ends to a mesh. Once the present row has been threaded into mesh 200, the operator may emplace cover 102 to extend over the attached SIC while still leaving the other row of holes 128 available for threading another SIC. Cover 102 may be incrementally advanced after each SIC is emplaced so as to provide shielding between each attached SIC 10 and the operator.

Figure 13:
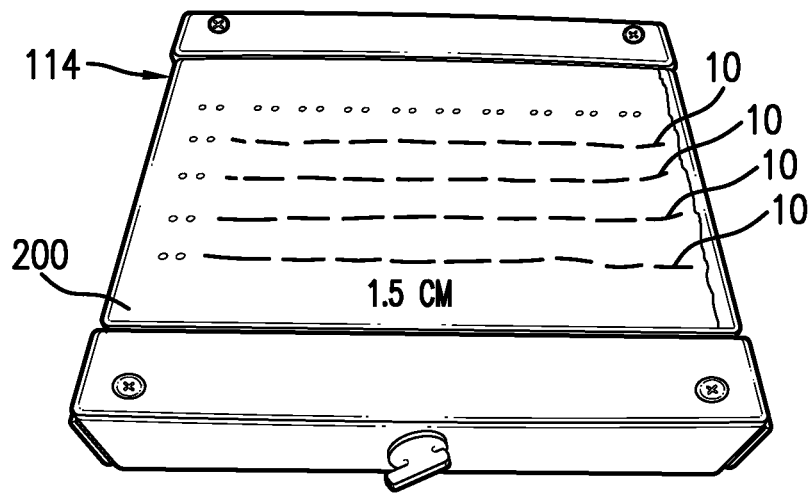
FIG. 13 depicts a completed mesh patch within the device.
Figure 14:
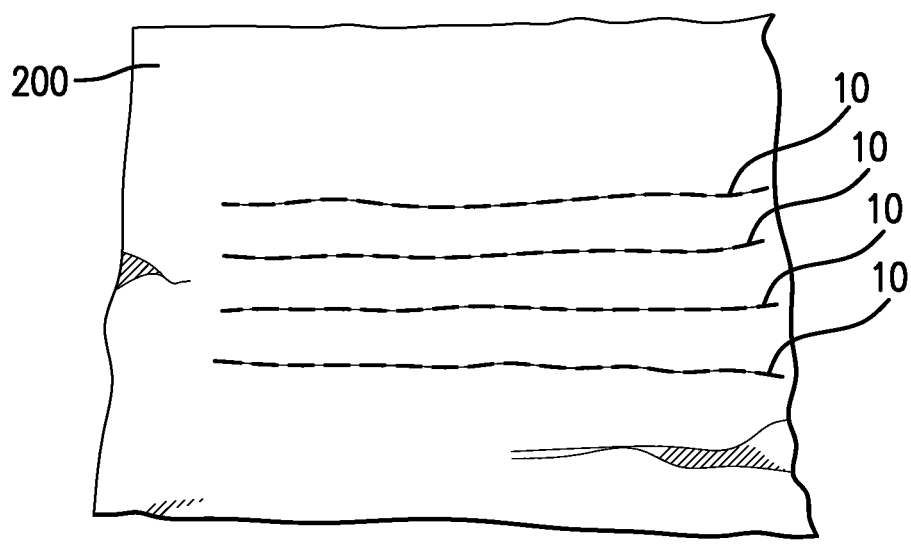
FIG. 14 depicts a completed mesh patch removed from the device.

FIGS. 13 and 14 depict mesh 200 after sewing subsequent rows of SIC 10 into mesh 200. This particular sewn mesh includes 4 rows of 10 seeds spaced at 1.5 cm between rows and 1 cm between seed deposit spots. Any of these dimensions can be accommodated by a properly formed tray 114 so as to meet the requirements of the user physician for implantation.

FIG. 14 depicts a finished mesh 200 removed from tray 114. Cam knobs 150 and 152 will be turned to urge clamps 146 and 148 from ridges 105 and 107 respectively and thus allow for mesh 200 to be removed from product 100. If desired, it is possible to instead score the mesh material, with a scalpel, and remove a smaller finished mesh patch from the portion still clamped by device 100. The scalpel may be provided with the device, or even operably-received into cam-activated hold-down mechanism. Alternatively, after preparation, a scalpel blade can be moved horizontally across the mesh directly in front of the hold-down clamps so as to cut the prepared mesh out of the array preparation device. Still further, the operator has the option of replacing cover 102 over as shown in FIG. 1 so that the finished mesh 200 remains in protective shielding until subsequent removal for its clinical application.

Figure 15:
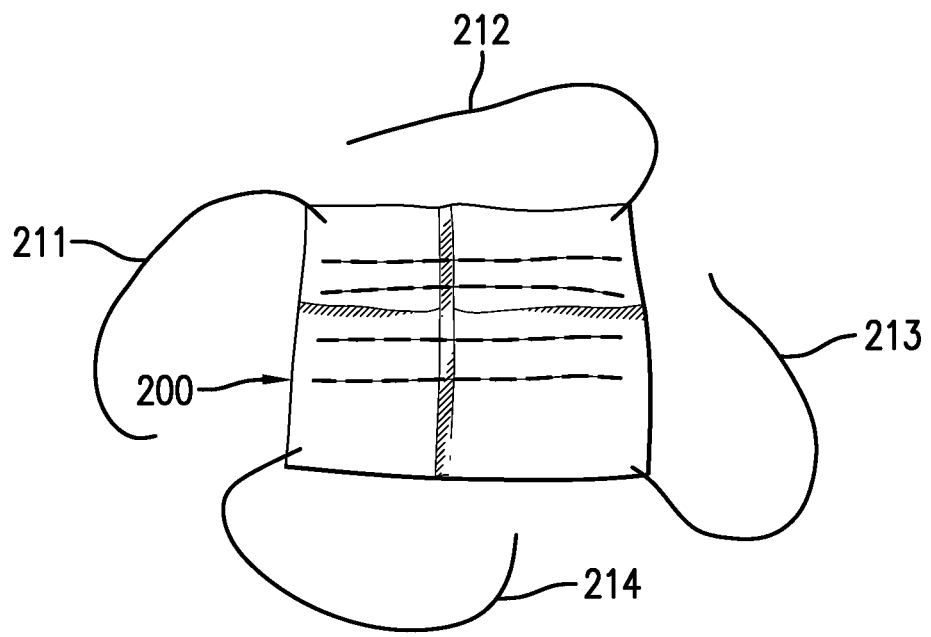
FIG. 15 depicts corner tails secured to a mesh as may be employed in a mesh formed by the present invention.

FIG. 15 depicts the finished mesh product 210 of the present invention having the number of SIC's and properly-arranged seeds 12 in place. Mesh product 210 further includes four elongate corner suture tails 211-214 attached thereto. It is contemplated that each of suture tails 211-214 may be threaded through an aperture on mesh 200 formed in accordance with the present invention. That is, tray 114 may further include properly positioned apertures to provide for the holes at each corner of mesh 200 for the suture tails 211-214. It is additionally contemplated that an operator may simply use one of the provided apertures 128 for punching the suture tail holes at its respective corner once mesh 200 has been at least partially released from device 100. It is further contemplated that array preparation device 100 may further provide apertures for securing a center tail of suture (not shown) for suturing the mesh into the patient.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A device for preparing a brachytherapy array comprising:
    a device body having a pair of elongate ridges in facing opposition and defining an elongate open channel communicating between opposed open ends thereof, each ridge including opposed ends and an elongate body extending therebetween, each opposed end of each ridge being positioned adjacent one of the opposed open ends of the elongate open channel;
    an elongate planar tray removably positionable in said open channel and having a working area defining a first array of apertures, said tray including first and second opposed major faces, said first major face defining at least three rows of apertures, and
    a holding mechanism for holding a planar surgical mesh over at least some of the apertures and disposed on at least one ridge and extending along the elongate body of the at least one ridge of said pair of ridges.

2. A device of claim 1 wherein said at least three rows of apertures consists of a number of pairs of apertures spaced apart by a distance at least of a length of a brachytherapy seed.

3. A device of claim 2, wherein each said pair of apertures is at least 1.2 centimeters apart.

4. A device of claim 2, wherein each said pair of apertures is at least 1.5 centimeters apart.

5. A device of claim 1, wherein said apertures of said first array do not communicate fully through said tray.

6. A device of claim 5, wherein said second major face defines a second array of apertures which do not communicate fully through said tray.

7. A device of claim 1, wherein said holding mechanism further comprises a mechanism for clamping at least one edge of the mesh to be prepared using said device.

8. A device of claim 1, wherein said device body and said tray include cooperating detents for removably holding said tray in said open channel.

9. A device of claim 1, further comprising a shield formed of a radiation-attenuating material for enclosing said tray.

10. A device of claim 9 wherein said shield comprises a cooperating removable cover.

11. A device of claim 10 wherein said removable cover is adapted to incrementally cover portions of said working area of said tray.

12. A device of claim 10, further comprising a punch tool storable within said device.

13. A method for forming a brachytherapy array, comprising the steps of:
    providing a device of claim 1;
    placing a planar surgical mesh on said tray of said device;
    holding said surgical mesh on said tray;
    punching at least one hole through said surgical mesh corresponding to one of said apertures of said tray;
    threading an elongate brachytherapy strand through said at least one hole punched in said punching step;
    affixing said strand to said surgical mesh.

14. A method of claim 13, further comprising the step of incrementally covering said working area after said affixing step.

15. A method of claim 13, further comprising the step of enclosing said surgical mesh within a radiation-attenuating shield.

16. A method of claim 13, further comprising the step of removing said surgical mesh from said device.

17. A device of claim 1, wherein said holding mechanism comprises a mechanism for clamping that is urgeable toward and away form the at least one ridge so as to be capable of holding and releasing the planar surgical mesh.

\* \* \* \* \*